(12) United States Patent
Kyslik et al.

(10) Patent No.: US 8,039,604 B2
(45) Date of Patent: Oct. 18, 2011

(54) DNA SEQUENCE ENCODING PENICILLIN ACYLASE, NOVEL RECOMBINANT RECOMBINANT DNA CONSTRUCTS AND RECOMBINANT MICROORGANISMS

(75) Inventors: Pavel Kyslik, Prague (CZ); Vaclav Stepanek, Praha 5-Kosire (CZ); Lenka Hollerova, Prague (CZ); Stanislav Becka, Prague (CZ); Vyasarayani Williams Rajasekar, Thane (IN); Datla Anupama, Mumbai (IN); Kamila Plhackova, Praha 8-Kobylisy (CZ); Jaroslav Marsalek, Kourim (CZ)

(73) Assignees: Fermenta Biotech Limited, Maharashtra (IN); Mikrobiologicky UTSAV AV CR, Prague (CZ)

( * ) Notice: Subject to any disclaimer, the term of this patent is extended or adjusted under 35 U.S.C. 154(b) by 184 days.

(21) Appl. No.: 12/524,713

(22) PCT Filed: May 15, 2007

(86) PCT No.: PCT/IN2007/000193
§ 371 (c)(1),
(2), (4) Date: Jul. 27, 2009

(87) PCT Pub. No.: WO2008/093351
PCT Pub. Date: Aug. 7, 2008

(65) Prior Publication Data
US 2010/0112673 A1    May 6, 2010

(30) Foreign Application Priority Data
Jan. 31, 2007  (CZ) ...................... 2007-82

(51) Int. Cl.
*C07H 21/02* (2006.01)
*C07H 21/04* (2006.01)
*C12P 1/00* (2006.01)

(52) U.S. Cl. ....... 536/23.7; 536/23.1; 435/41; 435/69.1; 435/230; 435/320.1

(58) Field of Classification Search ................ 536/23.1, 536/23.7; 435/41, 69.1, 230, 320.1
See application file for complete search history.

(56) References Cited

U.S. PATENT DOCUMENTS

| | | |
|---|---|---|
| 3,871,962 A | 3/1975 | Kutzbach |
| 5,753,458 A | 5/1998 | Clausen et al. |
| 5,801,011 A | 9/1998 | Gardner |
| 5,850,019 A | 12/1998 | Maiti et al. |

FOREIGN PATENT DOCUMENTS

| | | |
|---|---|---|
| CZ | 244343 | 11/1984 |
| CZ | 246957 | 10/1987 |
| CZ | 291154 | 12/2002 |
| EP | 0 638 649 B1 | 2/1995 |
| WO | WO 97/04086 | 2/1997 |
| WO | WO 98/04732 | 2/1998 |

OTHER PUBLICATIONS

EMBL, Accession No. AY919310, 2005.*
Alvaro, G. et al., Apr. 1992, "Penicillin G Acylase from Kluyvera Citrophila: New Choice as Industrial Enzyme," Biotechnology Letters 14(4): 285-290.
Barbero, J. et al., 1986, "Complete nucleotide sequence of the penicillin acylase gene from Kluyvera citrophila," Gene 49:69-80.
Chiang, C. and Bennett, R.E., Jan. 1967, "Purification and Properties of *Penicillin amidase* from *Bacillus megaterium*," Journal of Bacteriology 93(1):302-308.
Cai, G. et al., May 2004, "Cloning, overexpression, and characterization of a novel thermostable *Penicillin G acylase* from *Achromobacter xylosoxidans*: probing the molecular basis for its high thermostability," Applied and Environmental Microbiology, 70(5):2764-2770.
Database EMBL [Online], Sep. 1, 2005, "*Achromobacter* sp. CCM 4824 *Penicillin G acylase* (pga) gene, complete cds," XP002473791, EBI accession No. EMBL: AY919310, Database accession No. AY919310.
Database EMBL [Online], Apr. 24, 2003, "*Achromobacter xylosoxidans penicillin G acylase* gene, complete cds," XP002473792, DBI accession No. EMBL: AF490005, Database accession No. AF490005.
Daumy, G.O. et al., Oct. 1986, "Expression and Regulation of the *Penicillijn G acylase Gene* from *Proteus rettgeri* Cloned in *Escherichia coli*," Journal of Bacteriology, 168(1): 431-433.
Hernández-Jústiz, O. et al., 1999, "Evaluation of different enzymes as catalysts for the production of β-lactam antibiotics following a kinetically controlled strategy," Enzyme and Microbial Technology 25: 336-343.

(Continued)

*Primary Examiner* — Rodney P. Swartz
(74) *Attorney, Agent, or Firm* — Law Offices of Albert Wai-Kit Chan, PLLC

(57) ABSTRACT

The invention consists in a nucleotide sequence having the size of (2646) bp, wherein the order of nucleotides is identical to the order of the nucleotide sequence encoding penicillin acylase from *Achromobacter* sp. CCM 4824 (formerly *Comamonas testosteroni* CCM 4824), eventually of the fragments of this sequence having the length of at least 150 nucleotides. The sequence can be used in the formation of a DNA construct, eventually the construct having at least one regulatory sequence regulating the expression of the gene and the production of a polypeptide with the penicillin acylase activity. The sequence can form part of a recombinant expression vector, which consists of the above-mentioned construct, promoter, translational start signal, translational and transcriptional stop signal. Further, the invention concerns a recombinant host cell, containing the nucleic acid construct carried by the vector or integrated into the cell chromosome, and the *E. coli* BL21 strain containing said sequence of the nucleotides encoding the penicillin acylase carried in the pKXIP1, the pKLP3 or the pKLP6 plasmid.

10 Claims, 5 Drawing Sheets

OTHER PUBLICATIONS

Illanes, A. et al., 1994, "Production of *Penicillin acylase* from *Bacillus megaterium* in Complex and Defined Media," Process Biochemistry 29:263-270.

Konstantinović, M. et al., 1994, "The *Penicillin amidase* of *Arthrobacter viscosus* (ATCC 15294)," Gene 143: 79-83.

Ljubijankić, G. et al., 1992, "The primary structure of *Providencia rettgeri penicillin G amidase* gene and its relationship to other gram negative amidases," DNA Sequence-Journal of DNA Sequencing and Mapping, 3:195-200.

Maresová, H. et al., Oct. 5, 2001, "A chemostat culture as a tool for the improvement of a recombinant *E. coli* strain over-producing *Penicillin G acylase*," Biotechnology and Bioengineering 75(1): 46-52.

Meevootisom, V. and Saunders, J,R., 1987, "Cloning and expression of *Penicillin acylase* genes from overproducing strains of *Escherichia coli* and *Bacillus megaterium*," Applied Microbiology and Biotechnology, 25:372-378.

Ohashi, H. et al., Nov. 1988, "Molecular Cloning of the *Penicillin G acylase* Gene from *Arthrobacter viscosus*," Applied and Environmental Microbiology 54(11): 2603-2607.

Ohashi, H. et al., Jun. 1989, "Expression of the *Arthrobacter viscosus Penicillin G Acylase* Gene in *Escherichia coil* and *Bacillus subtilis*," Applied and Environmental Microbiology 55(6): 1351-1356.

Plháčková, K. et al., Oct. 2003, "Isolation and characterization of a new strain of *Achromobacter* sp. with beta-lactam antibiotic acylase activity," Applied Microbiology and Biotechnology 62(5-6): 507-516.

Robak, M. and Szewczuk, A., 1981, "*Penicillin amidase* from *Proteus rettgeri*," Acta Biochimica Polonica, 28(3,4): 275-284.

Shimizu, M. et al., 1975, "Search for Microorganisms Producing *Cephalosporin acylase* and Enzymatic Synthesis of Cephalosporins," Agricultural and Biological Chemistry 39(6): 1225-1232.

Skrob, F. et al., May 20, 2003, "Novel *Penicillin G acylase* from *Achromobacter* sp. CCM 4824," Enzyme and Microbial Technology, 32(6): 738-744.

Verhaert, R.M.D. et al., Sep. 1997, "Molecular Cloning and Analysis of the Gene Encoding the Thermostable *Penicillin G acylase* from *Alcaligenes faecalis*," Applied and Environmental Microbiology, 63(9):3412-3418.

PCT International Search Report issued for Fermenta Biotech Ltd. et al., Int'l Application No. PCT/IN2007/000193, Filed May 15, 2007, Dated Mar. 25, 2008.

Written Opinion of the International Searching Authority for Fermenta Biotech Ltd. et al., Int'l Application No. PCT/IN2007/000193, Filed May 15, 2007.

Notification of Transmittal of the International Preliminary Report on Patentability (IPER) for Fermenta Biotech Ltd. et al., Int'l Application No. PCT/IN2007/000193, Filed May 15, 2007, Dated May 8, 2009.

* cited by examiner

*Achromobacter* sp. chromDNA x *Sau*3AI + pK19 x *Bam*HI pKAGSau401 x *Pst*I + pK19 x *Pst*I

FIGURE 5

```
cggagacaga ttcaatgaag cagcaatggt tgtcggccgc cctgttggcg gccagttcgt      60
gcctgcccgc gatggcggcg cagccggtgg cgccagccgc cggccagacg tccgaggcgg     120
ttgcggcacg gccccaaacc gccgatggca aggtcacgat ccggcgcgat gcctacggca     180
tgccgcatgt ctatgccgac acggtgtacg gcatcttcta cggctacggc tacgcggtgg     240
cgcaggaccg gctgttccag atggagatgg cgcggcgcag cacccagggc cgggtggccg     300
aggtgctggg cgcctcgatg gtgggcttcg acaagtcgat ccgcgccaat tcctcgcccg     360
agcgcatcca gcgccagttg gcggcgctgc cggccgccga ccgccaggtg ctggacggct     420
acgcggctgg catgaacgcc tggctggcgc gggtgcgggc ccagccgggc caactgatgc     480
ccaaggaatt caatgacctg ggtttcgcgc cggccgactg gaccgcctac gacgtggcga     540
tgatcttcgt cggcaccatg gccaaccgct tttcggacgc caacagcgag atcgacaacc     600
tggcgctgct gacggcgttg aaggaccggc atggcgccgc cgatgccatg cgcatcttca     660
accagttgcg ctggctgacc gacagccgcg cgccgaccac ggtgccggcc gaagcgggca     720
gctaccagcc gccggtgttc cagccggacg gcgcggaccc gctggcctac gcgctgccgc     780
gctacgacgg cacgccgccg atgctcgagc gggtggtgcg cgaccgggcc acgcggggcg     840
tggtcgacgg cgcgccggcg acgctgcggg cgcaactggc cgcccaatac gcgcaatcgg     900
gccagcccgg catcgccggc tttccgacca ccagcaatat gtggatcgtg ggccgcgacc     960
acgccaagga cgcgcgctcg atcctgctga acggcccgca gttcggctgg tggaatccgg    1020
cctataccta cggcatcggc ttgcacggcg ccggcttcga cgtggtcggc aacacgccgt    1080
tcgcctatcc cagcattctg ttcggccaca atgcacacgt gacgtggggt tcgaccgcgg    1140
gcttcggcga tgacgtcgac atctttgccg aaaagctcga tcccgccgac cgcacgcgct    1200
atttccacga cggccaatgg aagacgctgg aaaagcgcac cgacctgatc ctggtgaagg    1260
acgcggcgcc agtgacgctg gacgtgtacc gcagcgtgca tggcctgatc gtcaagttcg    1320
acgacgcgca gcacgtggcc tacgccaagg cgcgcgcctg ggaaggctat gaactgcaat    1380
cgctgatggc ctggacccgc aagacgcaat cggccaactg gaacagtgg aaggcgcagg     1440
cggcgcgcca tgcgctgacc atcaactggt actacgccga cgaccgcggc aacattggct    1500
acgcgcacac gggcttctat cccaggcgcc gtccgggcca cgatccgcgc ctgccggtgc    1560
ccggcaccgg cgagatggac tggctgggcc tgctgccgtt ctctaccaat ccgcaggtct    1620
acaacccgcg ccagggcttc atcgccaact ggaacaacca gccgatgcgc ggctacccgt    1680
ccaccgacct gttcgccatc gtctggggcc aggccgaccg ctacgccgag atcgagacgc    1740
gcctgaaggc catgaccgcg aacggaggca aggtcagcgc gcagcagatg tgggacctga    1800
tccgcaccac cagctacgcc gacgtcaacc gccgtcattt cctgccgttc ctgcaacgcg    1860
cggtgcaagg gctgccggcg gatgatccgc gcgtgcgcct ggtggccggc ctggcggcct    1920
gggacggcat gatgaccagc gagcgccaac cgggttactt cgacaacgcc ggcccggcgg    1980
tcatggacgc gtggctgcgc gccatgctgc ggcgcacgct ggccgacgag atgccggccg    2040
acttcttcaa gtggtacagc gccaccggct acccgacacc gcaggcgccg gccaccggtt    2100
cgctcaacct gaccaccggc gtcaaggtgc tgttcaacgc cctggccggg cccgaggctg    2160
gcgtgccgca gcgctatgac ttcttcaacg gcgcgcgcgc cgacgacgtc atcctcgcgg    2220
cgctggacga tgcgctggcg gcgctgcgcc aggcctatgg ccaggatccg gcggcatgga    2280
agatcccggc gccgccgatg tgttcgcgc caagaacttc ctgggcgtg ccgcaggccg       2340
acgccaaggc ggtgctgtgc tatcgggcca cgcagaaccg cggcaccgag aacaacatga    2400
cggtgttcga cggtaaatcg gtgcgcgcgg tggatgtggt ggcgccgggg cagagcggct    2460
tcgtcgcccc ggacggcacg ccgtcgccgc acacccgcga ccagttcgac ctgtacaaca    2520
ccttcggcag caaacgggtg tggttcacgg ccgatgaggt gcggcgcaac gctacgtcgg    2580
aagagacgtt gcgctacccg cggtaaggtc gcgcgcgccc tggtggctgg caagcctgca    2640
gtacac (SEQ ID NO:1)                                                 2646
```

US 8,039,604 B2

DNA SEQUENCE ENCODING PENICILLIN ACYLASE, NOVEL RECOMBINANT RECOMBINANT DNA CONSTRUCTS AND RECOMBINANT MICROORGANISMS

This application is the National Stage of International Application No. PCT/IN2007/000193, filed May 15, 2007, which claims priority of Czech Republic Application No. PV 2007-82, filed Jan. 31, 2007, the entire disclosures of which are incorporated by reference herein in their entirety.

TECHNICAL FIELD

The invention relates to a DNA sequence encoding the polypeptide penicillin acylase, novel recombinant DNA constructs and recombinant microorganisms carrying this sequence.

BACKGROUND ART

Penicillin acylases (E.C. 3.5.1.11, penicillin amidohydrolase) are produced by bacteria, actinomycetes, fungi and yeast. These important industrial enzymes are on the basis of their substrate specificity divided into three groups: penicillin G acylases (PGA), penicillin V acylases (PVA) and ester hydrolases of α-amino acids (AEH, formerly named ampicillin acylases). The enzymes of the PGA group have broad substrate specificity and catalyse the hydrolysis of the amidic bond of penicillins and cephalosporins. Among the bacterial producers of the PGA belong the species of the genera: *Achromobacter, Alcaligenes, Arthrobacter, Bacillus, Corynebacterium, Escherichia, Erwinia, Flavobacterium, Kluyvera, Micrococcus, Nocardia, Proteus, Providencia, Pseudomonas, Sarcina, Xanthomonas, Xylella* (Process Biochem. 24:146-154, 1989, Process Biochem. 27:131-143, 1992, Biotechnol. Adv. 18:289-301, 2000).

Apart from the production strains expressing PGA, obtained by the mutagenesis, recombinant microorganisms containing recombinant plasmids with the structural gene encoding PGA were prepared from *Escherichia coli* (CS 244 343 and CS 246 957), *Alcaligenes* sp. or *fecalis* (Current Microbiology 39:2444-2448, 1999; EP 638649, Appl. Environ. Microbiol. 63: 3412-3418, 1997), *Arthrobacter viscosus* (Appl. Environ. Microbiol. 54: 2603-2607, 1988 a 55: 1351-1356, 1989; Gene 143: 79-83, 1994), *Bacillus megaterium* (J. Bacteriol. 93: 302-306, 1967, Appl. Microbiol. Biotechnol. 25: 372-378, 1987; U.S. Pat. No. 3,145,395; Process Biochemistry 29: 263-270, 1994), *Kluyvera citrophila* (Agric. Biol. Chem. 39: 1225-1232, 1975; Gene 49: 69-80, Biotechnol. Letters 14: 285-290, 1992), *Providencia rettgeri* (Acta Biochim. Polonica 28: 275-284, 1981; J. Bacteriol. 168: 431-433, 1986; DNA sequences 3: 195-200, 1992).

Most prokaryotic producers of the PGA are gram-negative bacteria and the enzyme is located in the periplasma of the cell. In the *Bacillus megaterium* culture, the enzyme is secreted from the cell to the medium.

The penicillin G acylases are industrially used mainly for the hydrolysis of the phenylacetyl derivatives of cephalosporins and penicillin G for the purpose of the preparation of the intermediates 6-APA and 7-ADCA. At present, these enzymes are used also in synthetic reactions, in the acylations of the above-mentioned intermediates, leading to the preparation of semi-synthetic antibiotics (e.g., U.S. Pat. No. 5,753,458 and U.S. Pat. No. 5,801,011; WO 98/04732; WO 97/04086; Enzyme Microb. Technol. 25: 336-343, 1999; Synthesis of β-lactam antibiotics: Chemistry, Biocatalysis and Process Integration, Ed.: A. Bruggink, Kluwer Academic Publishers, Dordrecht/Boston/London, 2001).

For a repeated, long-term use of the PGA in the catalysis of the enzyme reaction, the enzyme is stabilized by immobilization or encapsulation, forming an enzyme catalyst. In this form, the enzyme shows a higher pH stability, temperature stability and a longer half-life period under the reaction conditions, under which it catalyzes the course of the reaction.

DISCLOSURE OF THE INVENTION

Object of the present invention is a nucleotide sequence having the size of 2646 bp, wherein the order of nucleotides is at least 95% identical to the order of nucleotides shown in FIG. 5.

The aspect of the present invention are further fragments of the nucleotide sequence of the present invention, encoding penicillin acylase, having the length of at least 150 nucleotides.

A further aspect of the present invention is a nucleic acid construct containing the nucleotide sequence of the present invention or the fragment of the nucleotide sequence of the present invention, having at least one regulatory sequence regulating the expression of the gene and the production of the polypeptide having the penicillin acylase activity.

Another aspect of the present invention is a recombined plasmid containing the sequence of nucleotides of the present invention or the fragment of the sequence of the present invention.

A further aspect of the present invention is a recombinant expression vector consisting of the nucleic acid construct of the present invention, promoter, translational start signal and translational and transcriptional stop signal.

Another aspect of the present invention is a host cell containing the nucleic acid construct of the present invention. In this host cell, the nucleic acid construct can be carried in the recombinant expression vector of the present invention or it can be integrated in the cell genome.

Yet another aspect of the present invention are recombined plasmids pKX1P1, pKLP3 and pKLP6, characterized by the inserted nucleotide sequence of the present invention, isolated from the strain *Achromobacter* sp., and by the restriction map according to FIGS. 1 and 2.

A further aspect of the present invention is a strain *Escherichia coli* BL21 containing the sequence of the present invention, carried by the plasmids pKX1P1, pKLP3 or pKLP6.

The basis of the present invention is the nucleotide sequence having the size of 2646 bp, wherein the order of nucleotides is identical to the order of nucleotides shown in FIG. 5, eventually the fragments of this sequence, encoding penicillin acylase, having the length of at least 150 bases. Said sequence can form part of DNA constructs, recombinant plasmids and vectors. By a suitable vector, said sequence can be inserted into the genome of a bacterial or yeast host, which can then be used for the production of penicillin acylase.

One of the possible embodiments of the present invention is the strain *Escherichia coli* BL21(pKX1P1) (CCM 7394) containing the recombinant plasmid pKX1P1, prepared on the basis of the nucleotide sequence of the newly isolated structural gene having the penicillin acylase activity. Said plasmid is characterized by the insertion of the DNA fragment having the size of 2646 bp (including the region with the SD sequence) into the plasmid vector pK19 (R. D. Pridmore, Gene 56: 309-312, 1987), and the restriction map shown in FIG. 1. The preparation of this recombinant microorganism consisted in the isolation of the chromosomal DNA from the cells of the strain *Achromobacter* sp. CCM 4824 (originally

*Comamonas testosteroni* CCM 4824; Plháčková et al., Appl. Microbiol. Biotechnol. 62: 507-516, 2003) and the preparation of the recombinant microorganism *E. coli* TOP10 (pKLP3) carrying a 5.1 kb fragment of the chromosomal DNA. The nucleotide sequence of the structural gene pga was obtained by the PCR technique (polymerase chain reaction) using the DNA of the plasmid pKLP3. In accordance with the determined NT sequence of the gene, DNA primers were proposed (Table 1), which were used for determining the complete nucleotide sequence of the gene, including the regulatory region with the SD sequence by the same PCR-sequencing technique. Based on the complete nucleotide sequence, the primers providing for the PCR-amplification of the whole structural gene for the penicillin acylase were proposed (PCR; W. Rychlik: Methods in Molecular Biology 15, 31-39, 1993). Chromosomal DNA of the strain *Achromobacter* sp. CCM 4824 was used as the template. The resulting PCR products were isolated and ligated into the multicopy plasmid pK19 (R. D. Pridmore, Gene: 309-312,1987), yielding recombinant plasmids, used subsequently for the transformation of the host strain *Escherichia coli* TOP10 (Invitrogen, USA.).

The preparation of the competent cells and the transformation of the host strains by the population of the recombinant plasmids was carried out according to H. Hanahan, J. Mol. Biol. 166: 557-580, 1983. From the grown colonies, the recombinant plasmids were isolated by the alkaline lysis method (H. C. Birnboim a J. Doly: Methods in Enzymology 100, 243-254, 1983) and the size of the inserted fragment and its orientation were determined.

In selected recombinant clones of the host TOP10, the activity of the enzyme penicillin acylase was tested in batch cultures in the LB medium. The recombinant plasmid isolated from the strain with the highest overall activity of the PGA was designated pKX1P1. From this plasmid construct, the pga gene is expressed constitutively. The host strain BL21 was subsequently transformed by this plasmid.

The resulting recombinant strain *Escherichia coli* carrying the plasmid pKX1P1 and producing penicillin acylase was cultivated in a stirred bioreactor. The optimum procedure is the cultivation of the strain on the mineral medium M9 supplemented with casein hydrolysate and glycerol as the source of carbon and energy. The fed batch cultivation was carried out at the temperature in the range of from 20 to 30° C., while the pH was maintained in the range of from 5.5 to 7.5 and the concentration of the oxygen dissolved in the medium was 10 to 40%.

BRIEF DESCRIPTION OF DRAWINGS

FIG. 5 represents the nucleotide sequence of the structural gene pga and the adjacent regions.

EXAMPLES

Example 1

Figure 1:
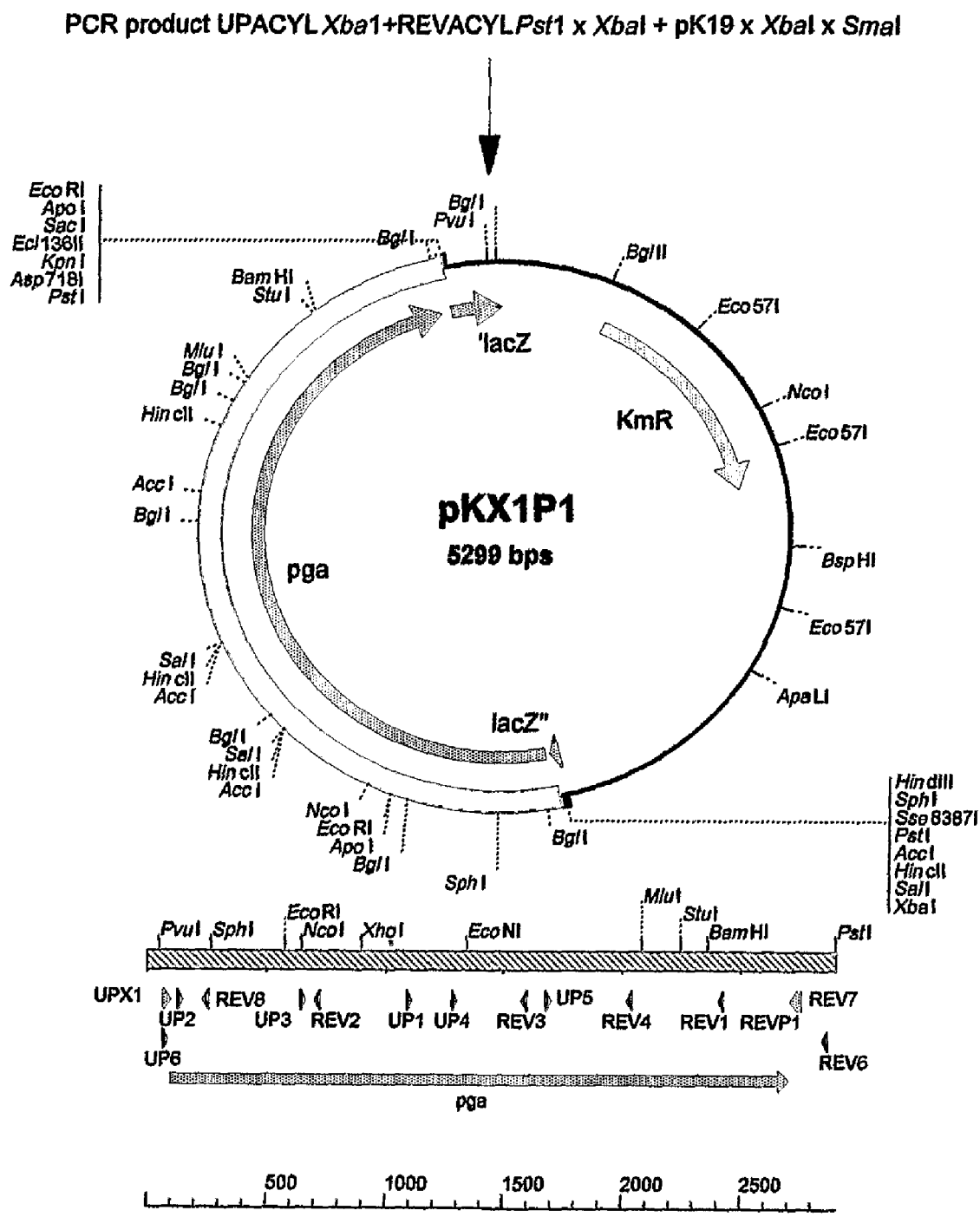
FIG. 1 represents the restriction map of the recombinant plasmid pKX1P1.

Cultivation of *A.* sp. and Isolation of the Chromosomal DNA

The soil isolate of *Achromobacter* sp. CCM 4824 (Škrob et al., Enzyme Microbiol. Technol. 32:738-744, 2003; Plháčková et al., Appl. Microbiol. Biotechnol. 62: 507-516, 2003) was cultivated in 50 ml of LB medium (in g/1: tryptone 10, yeast extract 5, NaCl 5; pH 7.2-7.5) at 37° C. on the rotating shaker (200 rpm) for 12-16 h. The biomass from 2 ml of the culture was isolated from the medium by centrifugation, washed with saline solution and stored at −20° C.

The chromosomal DNA was isolated from the de-frosted biomass by the commercially available columns GENOMIC-TIP 100/G (Qiagen, Switzerland) and the appropriate buffer kit GENOMIC BUFFER SET (Qiagen).

Example 2

Technology of the Recombinant DNA

All the methods of the DNA cleavage by the restriction enzymes (Fermentas, Lithuania), the analysis of the DNA molecules in 1.0% agarose gel (USB, U.S.A.) in the TBE buffer, the ligation by the T4 DNA ligase (Fermentas, Lithuania) were carried out in accordance with the standard protocols Molecular cloning: a laboratory manual. Eds: Sambrook J., Fritsch E. F., Maniatis T., 2nd edition, 1989, Cold Spring Harbor Laboratory Press, U.S.A.). For the PCR reactions and the DNA sequencing, the primers (Tab. 1) were synthesized by the companies MWG-Biotech AG (Germany) and Metabion (Germany). For carrying out the PCR reactions, the Thermocycler PTC-200 (MJ-Research, Inc., U.S.A.) was used, and all the reactions were carried out with Pwo SuperYield DNA Polymerase in the presence of GC-RICH Solution (ROCHE, Switzerland). The size of the products of the PCR technique was determined in 1% agarose gel in the TBE buffer, wherein the DNA of the phage λ cleaved by the restriction endonuclease PstI was used as the molecular weight standard. The specific products of the PCR intended for further subcloning or sequencing were isolated from the agarose gel with the QIAEX II Gel Extraction Kit (Qiagen, Germany) according to the manufacturer's instructions. The unique DNA fragments were purified by the High Pure PCR Product Purification Kit (ROCHE, Switzerland) according to the manufacturer's instructions. The preparation of competent cells and the transformation of the host strains were carried out according to J. Hanahan, Mol. Biol. 166: 557-580, 1983, wherein the competent cells, transformed by the plasmids carrying the desired PCR fragments, were cultivated for 16 h at 37° C. on the solid cultivation medium Luria-Bertani (LB, in g/l: tryptone 10, yeast extract 5, NaCl 5, agar 15; pH 7.2-7.5) supplemented with the antibiotic kanamycin (Km, 50 μg/ml), eventually in 50 ml of liquid LB medium supplemented with Km on the orbital shaker Gallenkamp (200 rpm). For subsequent analyses, the recombinant plasmids were isolated with the Qiagen Plasmid Midi Kit (Qiagen, Germany) and the High Pure Plasmid Isolation Kit (ROCHE, Switzerland) according to the manufacturer's instructions. The determination of all NT DNA sequences was carried out at the Institute of Microbiology AS CR automatically on the 3100 DNA Sequencer (Perkin-Elmer, U.S.A.). The obtained sequences were analyzed by the software Lasergene (DNASTAR Inc., U.S.A.). The homology of the NT sequences was verified by the software BLAST (National Center for Biotechnology Information, U.S.A.; S. F. Altschul et al.: Nucleic Acids Res. 25: 3389-3402, 1997).

(list of the primers—see Tab. 1). The nucleotide sequence of the structural gene pga having 2592 nucleotides (including the termination triplet TAA) shows in the region defined by the nucleotides 63 to 2592 92% identity to the pga gene of the related microorganism *Achromobacter xylosoxidans* ssp. *xylosoxidans* (GenBank AF490005).

TABLE 1

DNA primers and their location with regard to the pga gene

| Specific primer | Size (NTs) | Nucleotide sequences | Location |
|---|---|---|---|
| REVACYL1 | 18 | CGG CAC GCC CAG GAA GTT (SEQ ID NO: 2) | 2319 . . . 2302 |
| REVACYL2 | 20 | CGC CAT GCC GGT CCT TCA AC (SEQ ID NO: 3) | 622 . . . 603 |
| REVACYL3 | 21 | TGT GCG CGT AGC CAA TGT TGC (SEQ ID NO: 4) | 1495 . . . 1475 |
| REVACYL4 | 20 | GTT GGC GCT CGC TGG TCA TC (SEQ ID NO: 5) | 1936 . . . 1917 |
| REVACYL6 | 21 | CAC CGG ACC ACG CTG GTG ATC (SEQ ID NO: 6) | 2758 . . . 2738 |
| REVACYL8 | 22 | CAT CGC GCC GGA TCG TGA CCT T (SEQ ID NO: 7) | 157 . . . 136 |
| UPACYL1 | 20 | CAG TTC GGC TGG TGG AAT CC (SEQ ID NO: 8) | 985 . . . 1004 |
| UPACYL2 | 20 | CCT GTT GGC GGC CAG TTC GT (SEQ ID NO: 9) | 27 . . . 46 |
| UPACYL3 | 20 | CAT GGC CAA CCG CTT TTC GG (SEQ ID NO: 10) | 543 . . . 562 |
| UPACYL5 | 23 | GCC TGC TGC CGT TCT CTA CCA AT (SEQ ID NO: 11) | 1574 . . . 1596 |
| UPACYL6 | 20 | GGC GCG GAC CCA TTC GAT AC (SEQ ID NO: 12) | −33 . . . −14 |
| UPACYLXba1 | 28 | CGC GGA CCC ATT CTA GAC GGA GAC AGA T (SEQ ID NO: 13) | −31 . . . −4 |
| REVACYLPst1 | 28 | GTG TAC TGC AGG CTT GCC AGC CAC CAG G (SEQ ID NO: 14) | 2632 . . . 2605 |

Example 3

Figure 2:
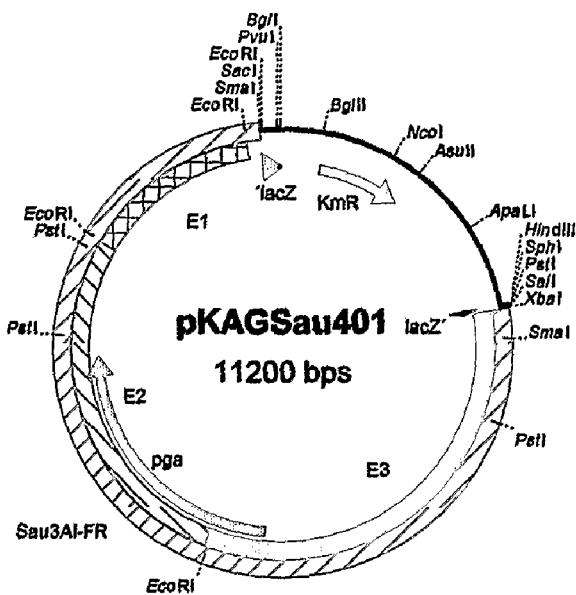
FIG. 2 represents plasmids pKAGSau401, pKLP3 and pKLP6.
Figure 2:
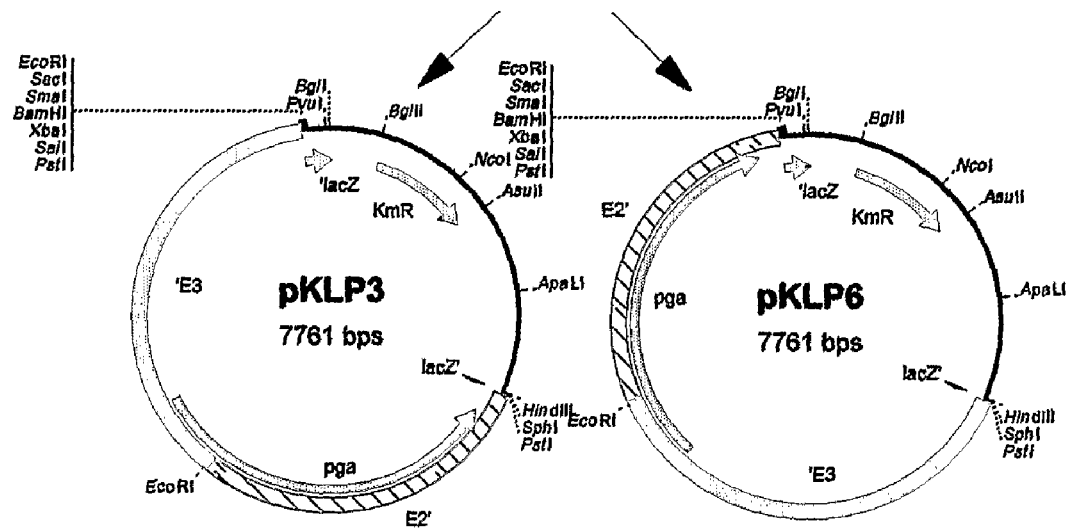

Determination of the Nucleotide Sequence of the pga Gene and Preparation of the Expression System The chromosomal DNA of the strain *Achromobacter* sp. CCM 4824 was partially cleaved by the enzyme Sau3AI. These DNA-fragments were ligated with the BamHI-linearized plasmid DNA of the vector pK19 (RD. Pridmore: Gene 56, 309-312, 1987). The resulting constructs were subsequently used for the transformation of the host strain *E. coli* TOP10. The plasmid pKAGSau401 (FIG. 2), isolated from the recombinant strain *E. coli* showing the penicillin acylase phenotype (PGA+), was subjected to the restriction by PstI. The largest PstI-fragment, ca 5.1 kb, was subsequently subcloned into the PstI-linearized vector pK19, forming 2 types of constructs, pKLP3 and pKLP6 (FIG. 2), with inversely oriented PstI-inserts. The recombinant strains *E. coli* TOP10 (pKLP3) and *E. coli* TOP10(pKLP6) had the phenotype PGA+.

The isolated plasmids pKLP3 and pKLP6 were used as the template for obtaining the complete nucleotide sequence of the pga gene with both universal M13/pUC sequencing primers and subsequently derived pga-strictly specific primers Based on the thus obtained nucleotide sequence of the pga gene including the adjacent regions, the primers were proposed, enabling the PCR amplification of the structural gene pga with the chromosomal DNA of the strain *Achromobacter* sp. CCM 4824 as the template. The proposed two primers UPACYLXba1 and REVACYLPst1 from the regions adjacent to the structural gene pga with inserted restriction sites XbaI, resp. PstI (Tab. 1) were used in the PCR reaction comprising the following steps: 1) 5 min at 94° C.; 2) 30 cycles with the denaturation at 94° C. for 45 s, binding of the primers at 60° C. for 45 s and the polymerization at 72° C. for 3 min; 3) completion of the polymerization at 72° C. for 10 min. Under these conditions, the specific PCR product of the size 2663 bp was prepared, carrying the whole structural gene pga including the preceding part of the regulatory region with the Shine-Dalgarno sequence. This pga-specific PCR product was subjected to the cleavage by the restriction endonuclease XbaI (target sequence in the UPACYLXba1 primer) and subsequently ligated into the vector pK19, cleaved by two polylinker enzymes XbaI and SmaI. The obtained recombinant construct was designated pKX1P1 plasmid (FIG. 1). The analysis of the DNA sequence of this plasmid has shown that during the insertion of the PCR-product, no insertion-deletion mutations have occurred, but the site mutation C→T at the 99th nucleotide of the structural gene pga in comparison with the originally postulated nucleotide sequence was found. However, this mutation is silent, because it does not change the amino acid type encoded by the triplet. The prototrophic host strain E. coli BL21 (Invitrogen, USA) was transformed by the isolated recombinant plasmids pKLP6 and pKX1P1 and the prokaryotic expression system BL21 (pKX1P1) for PGA was prepared.

Example 4

Expression of the pga in Escherichia Coli

Preparation of the Inoculum for the Cultivation of the Escherichia coli BL21 (pKX1P1) Strains From a glycerol conserve (grown culture mixed with glycerol according to Molecular cloning: a laboratory manual. Eds: Sambrook J., Fritsch E. F., Maniatis T., 2nd edition, 1989, Cold Spring Harbor Laboratory Press, U.S.A.) stored at −70° C., 50 ml of LB medium supplemented with kanamycin (Km, 50 μg/ml) was inoculated. The inoculum was cultivated for 16 h at 28° C. in the orbital incubator shaker Gallenkamp (200 rpm).

Cultivation in the Bioreactor

Figure 3:
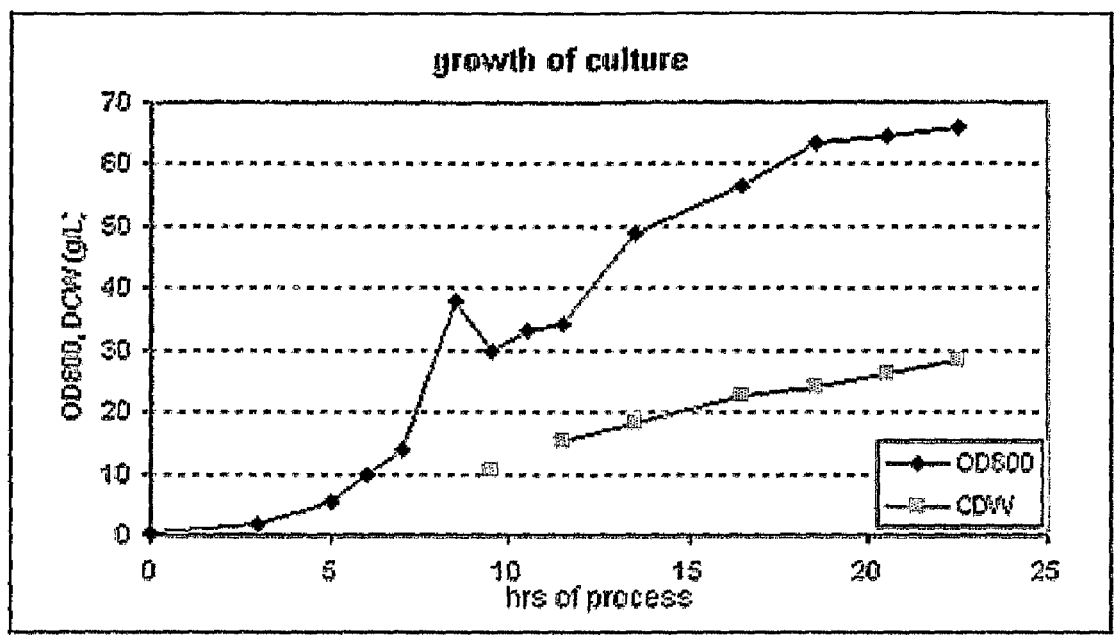
FIG. 3 represents the course of the optical density of the culture (OD600) and the dry weight of the cells (dry mass) (g/L) during the fed batch cultivation of the strain BL21 (pKX1P1) in the stirred bioreactor.
Figure 4:
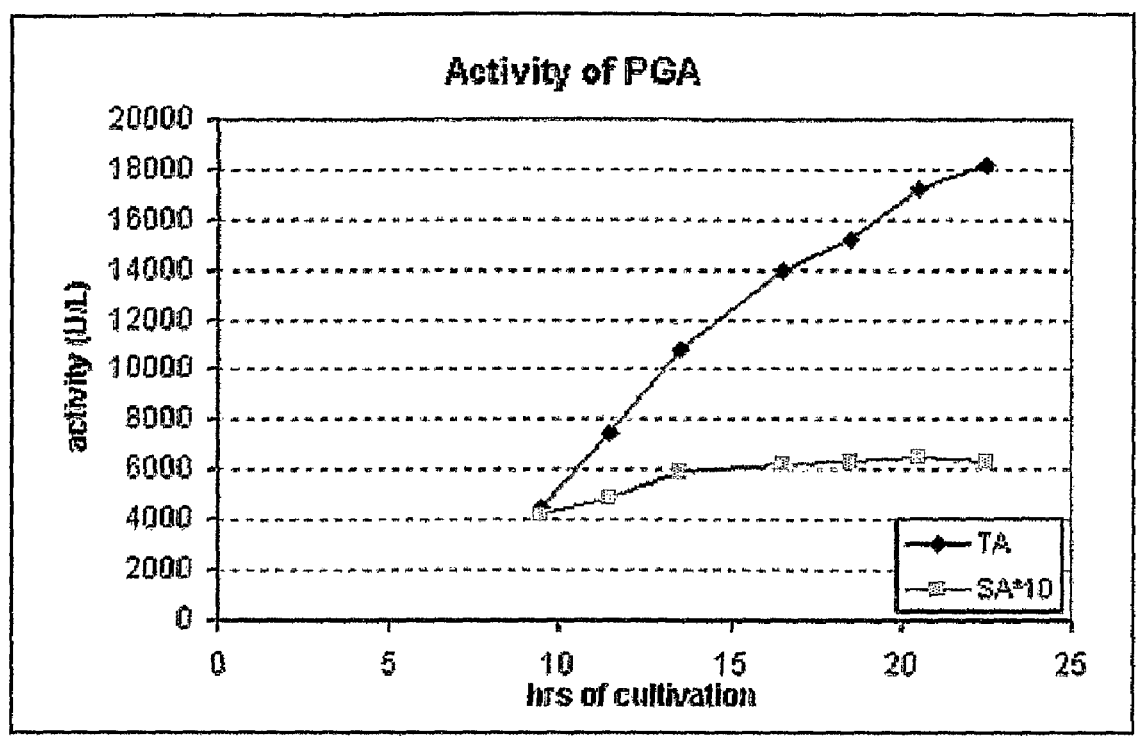
FIG. 4 represents the course of the total activity (TA) and the specific activity (SA) during the fed batch cultivation of the strain BL21(pKX1P1) in the stirred bioreactor.

The strain BL21 (pKX1P1) was cultivated under strictly defined conditions in the M9 medium (Tab. 2) supplemented with glycerol (5-25 g/l) and casein hydrolysate (5-25 g/l) as the carbon and energy sources in the stirred bioreactor Biostat MD (B. Braun Biotech Intl., Melsungen, Germany): working volume 8.2 l, air flow rate 8-9 l of air/min, initial stirring frequency 200 to 300 rpm, at the temperature in the range of from 20 to 28° C. The pH of the medium was maintained in the range of from 7.5 to 5.5 and the concentration of the dissolved oxygen ($pO_2$) was automatically maintained in the range of from 5 to 30% of the maximum oxygen saturation of the medium by adjusting the stirring frequency in the range of from 200 to 840 rpm. The cultivation ran for 20 to 25 hours as fed batch cultivation (FIGS. 3 and 4). At the end of the cultivations, the following parameters were determined: the biomass concentration (cell dry weight, cdw), the total activity (TA) and the specific activity (SA) of penicillin acylase.

The parameters were determined as follows:

biomass concentration: 28 g cdw/l of the cultivation medium total activity 18 000 U/l of the cultivation medium specific activity 670 U/g cdw Enzyme Activity Determination For determining the PGA enzyme activity, samples of the culture of the volume of 1 to 2 ml were taken from the production cultivation. The biomass was isolated by centrifugation and after washing with 1 to 2 ml of distilled water and further centrifugation it was stored at −20° C. The de-frosted biomass was resuspended in 0.005 M phosphate buffer (pH 8.0). The activity of the PGA was determined by the titration at 37° C. with penicillin G as the substrate.

TABLE 2

The components of the cultivation medium M9

| substance | formula | concentration (g/L) |
| --- | --- | --- |
| Ammonium sulphate | $(NH_4)_2SO_4$ | 4.0 |
| Potassium dihydrogen phosphate | $KH_2PO_4$ | 13.6 |
| Sodium chloride | NaCl | 10.0 |
| Sodium hydroxide | NaOH | 3.0 |
| Magnesium sulphate | $MgSO_4 \cdot 7 H_2O$ | 2.0 |
| Calcium chloride | $CaCl_2 \cdot 6 H_2O$ | 0.05 |
| Ferrous sulphate | $FeSO_4 \cdot 7 H_2O$ | 0.01 |

INDUSTRIAL USE

The recombinant strains of the microorganisms containing the nucleotide sequence of the present invention can be used in the production of penicillin acylase for various applications in the chemical and the pharmaceutical industry.

---

We claim:

1. An isolated nucleotide sequence which has the sequence of SEQ ID NO: 1, wherein the nucleotide sequence encodes penicillin acylase.

2. A recombinant plasmid comprising the nucleotide sequence of claim 1.

3. The recombinant plasmid of claim 2, wherein the plasmid has at least one regulatory sequence regulating the expression of the gene and the production of a polypeptide having penicillin acylase activity.

4. The recombinant plasmid of claim 3, wherein the regulatory sequence is selected from the group consisting of promoter, translational start signal, translational stop signal, transcriptional start signal, and transcriptional stop signal.

5. The recombinant plasmid of claim 2, wherein the plasmid is pKX1P1, pKLP3 or pKLP6.

6. A recombinant expression vector comprising the plasmid of claim 2.

7. A host cell comprising the plasmid of claim 2.

8. The host cell of claim 7, wherein the nucleotide sequence encoding penicillin acylase is integrated into the cell genome.

9. The host cell of claim 7, wherein the host cell is a strain of *Escherichia coli*.

10. The host cell of claim 9, wherein the strain is *Escherichia coli* BL21.

* * * * *

SEQUENCE LISTING

```
<160> NUMBER OF SEQ ID NOS: 1

<210> SEQ ID NO 1
<211> LENGTH: 2646
<212> TYPE: DNA
<213> ORGANISM: Artificial sequence
<220> FEATURE:
<221> NAME/KEY: misc_feature
<222> LOCATION: (1)..(2646)
<223> OTHER INFORMATION: Achromobacter Species CCM 4824; Recombinant DNA

<400> SEQUENCE: 1
cggagacaga ttcaatgaag cagcaatggt tgtcggccgc cctgttggcg gccagttcgt      60
gcctgcccgc gatggcggcg cagccggtgg cgccagccgc cggccagacg tccgaggcgg     120
ttgcggcacg gccccaaacc gccgatggca aggtcacgat ccggcgcgat gcctacggca     180
tgccgcatgt ctatgccgac acggtgtacg gcatcttcta cggctacggc tacgcggtgg     240
cgcaggaccg gctgttccag atggagatgg cgcggcgcag cacccagggc cgggtggccg     300
aggtgctggg cgcctcgatg gtgggcttcg acaagtcgat ccgcgccaat ttctcgcccg     360
agcgcatcca gcgccagttg gcggcgctgc cggccgccga ccgccaggtg ctggacggct     420
```

-continued

| | |
|---|---|
| acgcggctgg catgaacgcc tggctggcgc gggtgcgggc ccagccgggc caactgatgc | 480 |
| ccaaggaatt caatgacctg ggtttcgcgc cggccgactg daccgcctac gacgtggcga | 540 |
| tgatcttcgt cggcaccatg gccaaccgct tttcggacgc caacagcgag atcgacaacc | 600 |
| tggcgctgct gacggcgttg aaggaccggc atggcgccgc cgatgccatg cgcatcttca | 660 |
| accagttgcg ctggctgacc gacagccgcg cgccgaccac ggtgccggcc gaagcgggca | 720 |
| gctaccagcc gccggtgttc cagccggacg gcgcggaccc gctggcctac cgctgccgc | 780 |
| gctacgacgg cacgccgccg atgctcgagc gggtggtgcg cgacccggcc acgcggggcg | 840 |
| tggtcgacgg cgcgcggcg acgctgcggg cgcaactggc cgcccaatac gcgcaatcgg | 900 |
| gccagcccgg catcgccggc tttccgacca ccagcaatat gtggatcgtg ggccgcgacc | 960 |
| acgccaagga cgcgcgctcg atcctgctga acggcccgca gttcggctgg tggaatccgg | 1020 |
| cctataccta cggcatcggc ttgcacgcg ccggcttcga cgtggtcggc aacacgccgt | 1080 |
| tcgcctatcc cagcattctg ttcggccaca atgcacacgt gacgtggggt tcgaccgcgg | 1140 |
| gcttcggcga tgacgtcgac atctttgccg aaaagctcga tcccgccgac cgcacgcgct | 1200 |
| atttccacga cggccaatgg aagacgctgg aaaagcgcac cgacctgatc ctggtgaagg | 1260 |
| acgcggcgcc agtgacgctg gacgtgtacc gcagcgtgca tggcctgatc gtcaagttcg | 1320 |
| acgacgcgca gcacgtggcc tacgccaagg cgcgcgcctg ggaaggctat gaactgcaat | 1380 |
| cgctgatggc ctggacccgc aagacgcaat cggccaactg ggaacagtgg aaggcgcagg | 1440 |
| cggcgcgcca tgcgctgacc atcaactggt actacgccga cgaccgcggc aacattggct | 1500 |
| acgcgcacac gggcttctat cccaggcgcc gtccgggcca cgatccgcgc ctgccggtgc | 1560 |
| ccggcaccgg cgagatggac tggctgggcc tgctgccgtt ctctaccaat ccgcaggtct | 1620 |
| acaacccgcg ccagggcttc atcgccaact ggaacaacca gccgatgcgc ggctacccgt | 1680 |
| ccaccgacct gttcgccatc gtctgggggcc aggccgaccg ctacgccgag atcgagacgc | 1740 |
| gcctgaaggc catgaccgcg aacggaggca aggtcagcgc gcagcagatg tgggacctga | 1800 |
| tccgcaccac cagctacgcc gacgtcaacc gccgtcattt cctgccgttc ctgcaacgcg | 1860 |
| cggtgcaagg gctgccggcg gatgatccgc gcgtgcgcct ggtggccggc ctggcggcct | 1920 |
| gggacggcat gatgaccagc gagcgccaac cgggttactt cgacaacgcc ggcccggcgg | 1980 |
| tcatggacgc gtggctgcgc gccatgctgc ggcgcacgct ggccgacgag atgccggccg | 2040 |
| acttcttcaa gtggtacagc gccaccggct acccgacacc gcaggcgccg gccaccggtt | 2100 |
| cgctcaacct gaccaccggc gtcaaggtgc tgttcaacgc cctggccggg cccgaggctg | 2160 |
| gcgtgccgca gcgctatgac ttcttcaacg gcgcgcgcgc cgacgacgtc atcctcgcgg | 2220 |
| cgctggacga tgcgctggcg gcgctgcgcc aggcctatgg ccaggatccg gcggcatgga | 2280 |
| agatcccggc gccgccgatg gtgttcgcgc ccaagaactt cctgggcgtg ccgcaggccg | 2340 |
| acgccaaggc ggtgctgtgc tatcgggcca cgcagaaccg cggcaccgag aacaacatga | 2400 |
| cggtgttcga cggtaaatcg gtgcgcgcg tggatgtggt ggcgccgggg cagagcggct | 2460 |
| tcgtcgcccc ggacggcacg ccgtcgcgc acacccgcga ccagttcgac ctgtacaaca | 2520 |
| ccttcggcag caaacggggtg tggttcacgg ccgatgaggt gcggcgcaac gctacgtcgg | 2580 |
| aagagacgtt gcgctacccg cggtaaggtc gcgcgcgccc tggtggctgg caagcctgca | 2640 |
| gtacac | 2646 |